United States Patent [19]

Nozaki et al.

[11] Patent Number: 5,059,538
[45] Date of Patent: Oct. 22, 1991

[54] RECOMBINANT PLASMID INSERTED WITH HERPES SIMPLEX VIRUS GENE

[75] Inventors: Chikateru Nozaki; Hiroshi Nakatake; Yoichiro Kino; Tatsuo Eto; Keiichi Makizumi; Nobuya Ohtomo, all of Kumamoto, Japan

[73] Assignee: Juridical Foundation The Chemo-Sero-Therapeutic Research Institute, Kumamoto, Japan

[21] Appl. No.: 896,923

[22] Filed: Aug. 15, 1986

[30] Foreign Application Priority Data

Aug. 30, 1985 [JP] Japan .................................. 60-192916

[51] Int. Cl.$^5$ ........................ C12N 15/81; C12N 15/38
[52] U.S. Cl. .................................. 435/320.1; 435/942; 935/18
[58] Field of Search ...................... 435/68, 70, 91, 253, 435/235, 172.3, 317, 320, 317.1, 240.7; 536/27

[56] References Cited

U.S. PATENT DOCUMENTS

| | | | |
|---|---|---|---|
| 4,642,333 | 2/1987 | Person | 530/350 |
| 4,661,454 | 4/1987 | Botstein et al. | 435/266 |
| 4,738,926 | 4/1988 | Hamada et al. | 435/235 |
| 4,745,062 | 4/1988 | Guerineau et al. | 435/209 |

FOREIGN PATENT DOCUMENTS

170169  2/1986  European Pat. Off. .

OTHER PUBLICATIONS

Nakamura et al., *Gene*, 50 (1986) 239–245.
Izumoto et al. *Gene*, 59(1987) 151–159.
*Molecular and Cell Biology of Yeasts*, Ed. E. F. Walton et al., pp. 107, 108, 114.
Principles of Gene Manipulation, an Introduction to Genetic Engineering, Ed. Old et al. (1981), p. 163.
Bzik et al., "Nucleotide Sequence Specifying the Glycoprotein Gene, gB, of Herpes Simplex Virus Type 1", *Virology, vol. 133, 1984, pp. 301–314.*
Cappel et al., "Immune Response to a DNA Free Herpes Simplex Vaccine in Man", *Archives of Virology*, vol. 73, 1982, pp. 61–67.

*Primary Examiner*—Richard A. Schwartz
*Assistant Examiner*—S. L. Nolan
*Attorney, Agent, or Firm*—Wegner, Cantor, Mueller & Player

[57] ABSTRACT

A novel recombinant plasmid inserted with a herpes simplex virus gene, which comprises a plasmid vector containing a yeast DNA sequence and an *Escherichia coli* DNA sequence and carrying a promoter region and a herpes simplex virus gN gene (HSVgB) gene) recombined thereto under control of the promoter, said HSVgB gene lacking an N-terminal portion of the gene including a signal sequence-encoding region and optionally further lacking the region downstream therefrom, such as a gB gene lacking a DNA sequence encoding the N-terminal 30 amino acids, and a gB gene lacking a DNA sequence encoding the N-terminal 83 amino acids. The recombinant plasmid is useful for the production of transformed yeast, which is useful for the production of HSVgB proteins suitable for producing HSV vaccine and diagnostic reagents for herpes simplex virus infections.

2 Claims, 7 Drawing Sheets

Fig. 1 (A)

1-CTCGAGTTGCGCCGCCCGGACTGCAGCCGCCCGACCTCGAAGGTCGTTACCGTTACCCGCCCGGGTATATCTCACGTAGACTCCGACTGTCCGCTGG

101-TGGCCATCGTCGAGAGCGCCCCGACGGCTGTATCGGGCCCCGGTCGTGTGGTCTACGACGCCGACGTTTTCTGATCCTCTACTCGTCCTCCAGCA

201-CCTCGGCCCCCAGGCTACCTGACGGGGGGCACGACGGGCCCCCGTAGTCCCGCC

254-ATG CAC CAG GGC GCC CCC TCG TGG GGG CGC CGG TGG TTC GTC GTA TGG GCG CTC TTG GGG TTG ACG CTG GGG GTC
    Met-His-Gln-Gly-Ala-Pro-Ser-Trp-Gly-Arg-Arg-Trp-Phe-Val-Val-Trp-Ala-Leu-Leu-Gly-Leu-Thr-Leu-Gly-Val-25

329-CTG GTG GCG TCG GCG GCT CCG AGT TCC CCC GGC ACG CCT GGG GTC GCG CGC GAC CCA GGC GGC GAA CGG GGG CCC
    Leu-Val-Ala-Ser-Ala-Ala-Pro-Ser-Ser-Pro-Gly-Thr-Pro-Gly-Val-Ala-Arg-Asp-Pro-Gly-Gly-Glu-Arg-Gly-Pro-50

404-TGC CAC TCC GGC GCC GCC CTT GGC GCC GCC GCC CCA ACG GGG GAC CCA AAA CCG AAG AAG AAC AAA AAA CCG AAA
    Cys-His-Ser-Gly-Ala-Ala-Leu-Gly-Ala-Ala-Ala-Pro-Thr-Gly-Asp-Pro-Lys-Pro-Lys-Lys-Asn-Lys-Lys-Pro-Lys-75

Nae I
479-AAC CCA ACG CCA CCA CGC CCC GCC↓GGC GAC AAC GCG ACC GTC GCC GCG GGC CAC GCC ACC CTG CGC GAG CAC CTG
    Asn-Pro-Thr-Pro-Pro-Arg-Pro-Ala-Gly-Asp-Asn-Ala-Thr-Val-Ala-Ala-Gly-His-Ala-Thr-Leu-Arg-Glu-His-Leu-100

554-CGG GAC ATC AAG GCG GAG AAC ACC GAT GCA AAC TTT TAC GTG TGC CCA CCC CCC ACG GGC GCC ACG GTG GTG CAG
    Arg-Asp-Ile-Lys-Ala-Glu-Asn-Thr-Asp-Ala-Asn-Phe-Tyr-Val-Cys-Pro-Pro-Pro-Thr-Gly-Ala-Thr-Val-Val-Gln-125

629-TTC GAG CAG CCG CGC CGC TGC CCG ACC CGG CCC GAG GGT CAG AAC TAC ACG GAG GGC ATC GCG GTG GTC TTC AAG
    Phe-Glu-Gln-Pro-Arg-Arg-Cys-Pro-Thr-Arg-Pro-Glu-Gly-Gln-Asn-Tyr-Thr-Glu-Gly-Ile-Ala-Val-Val-Phe-Lys-150

Fig. 1 (B)

```
704- GAG AAC ATC GCC CCG TAC AAG TTC AAG GCC ACC ATG TAC TAC AAA GAC GTC ACC GTT TCG CAG GTG TGG TTC GGC
     Glu-Asn-Ile-Ala-Pro-Tyr-Lys-Phe-Lys-Ala-Thr-Met-Tyr-Tyr-Lys-Asp-Val-Thr-Val-Ser-Gln-Val-Trp-Phe-Gly-175

779- CAC CGC TAC TCC CAG TTT ATG GGG ATC TTT GAG GAC CGC GCC CCC GTC CCC TTC GAG GAG GTG ATC GAC AAG ATC
     His-Arg-Tyr-Ser-Gln-Phe-Met-Gly-Ile-Phe-Glu-Asp-Arg-Ala-Pro-Val-Pro-Phe-Glu-Glu-Val-Ile-Asp-Lys-Ile-200

854- AAC GCC AAG GGG GTC TGT CGG TCC ACG GCC AAG TAC GTG CGC AAC AAC CTG GAG ACC ACC GCG TTT CAC CGG GAC
     Asn-Ala-Lys-Gly-Val-Cys-Arg-Ser-Thr-Ala-Lys-Tyr-Val-Arg-Asn-Asn-Leu-Glu-Thr-Thr-Ala-Phe-His-Arg-Asp-225

929- GAC CAC GAG ACC GAC ATG GAG CTG AAA CCG GCC AAC GCC GCG ACG AGC CGG GGC TGG CAC ACC ACC GAC
     Asp-His-Glu-Thr-Asp-Met-Glu-Leu-Lys-Pro-Ala-Asn-Ala-Ala-Thr-Arg-Ser-Arg-Gly-Trp-His-Thr-Thr-Asp-250

1004- CTC AAG TAC AAC CCC TCG CGG TAC GAG GCG TTC CAC CGG ACG GTA AAC TGC ATC GTC GAG GAG GTG
      Leu-Lys-Tyr-Asn-Pro-Ser-Arg-Tyr-Glu-Ala-Phe-His-Arg-Thr-Val-Asn-Cys-Ile-Val-Glu-Glu-Val-275

1079- GAC GCG CGC TCG GTG TAC CCG GTG GAG TTT GTG CTG GCG ACT GGC GAC TTT GTG TAC ATG TCC CCG TTT TAC
      Asp-Ala-Arg-Ser-Val-Tyr-Pro-Val-Glu-Phe-Val-Leu-Ala-Thr-Gly-Asp-Phe-Val-Tyr-Met-Ser-Pro-Phe-Tyr-300

Sal I
1154- GGC TAC CGG GAG GGG TCG CAC ACC GAA CAC ACC ACG TAC GCC GCC GAC CGC TTC AAG CAG GTC GAC GGC TTC TAC
      Gly-Tyr-Arg-Glu-Gly-Ser-His-Thr-Glu-His-Thr-Thr-Tyr-Ala-Ala-Asp-Arg-Phe-Lys-Gln-Val-Asp-Gly-Phe-Tyr-325
```

Fig. 1 (C)

1229- GCG CGC GAC CTC ACC AAG GCC CGG GCC ACG GCG CCG ACC ACC CGG AAC CTG CTC ACG ACC CCC AAG TTC ACC
      Ala-Arg-Asp-Leu-Thr-Lys-Ala-Arg-Ala-Thr-Ala-Pro-Thr-Thr-Arg-Asn-Leu-Leu-Thr-Thr-Pro-Lys-Phe-Thr-350

1304- GTG GCC TGG GAC TGG GTG CCA AAG CGC CCG TCG GTC TGC ACC ATG ACC AAG TGG CAG GAA GTG GAC GAG ATG CTG
      Val-Ala-Trp-Asp-Trp-Val-Pro-Lys-Arg-Pro-Ser-Val-Cys-Thr-Met-Thr-Lys-Trp-Gln-Glu-Val-Asp-Glu-Met-Leu-375

1379- CGC TCC GAG TAC GGC GGC TCC TTC CGA TTC TCC TCC GAC GCC ATA TCC ACC ACC TTC ACC ACC AAC CTG ACC GAG
      Arg-Ser-Glu-Tyr-Gly-Gly-Ser-Phe-Arg-Phe-Ser-Ser-Asp-Ala-Ile-Ser-Thr-Thr-Phe-Thr-Thr-Asn-Leu-Thr-Glu-400

RECOMBINANT PLASMID INSERTED WITH HERPES SIMPLEX VIRUS GENE

The present invention relates to a novel recombinant plasmid inserted with a herpes simplex virus gene, i.e. a recombinant plasmid which is useful for the production of a herpes simplex virus protein which is in turn useful for the production of a herpes simplex vaccine effective for the prophylaxis of herpes simplex virus infections.

More particularly, the present invention relates to a recombinant plasmid which is obtained by inserting a specific gene (gB gene) of the herpes simplex virus (hereinafter, referred to as "HSV"), i.e. the HSVgB gene, into a shuttle vector downstream of the appropriate promoter region of the vector, wherein said vector can replicate in both *Escherichia coli* and yeast. The present invention further relates to a novel transformed yeast which is produced by transforming a yeast with said recombinant plasmid, and a method for producing HSV proteins, particularly HSV membrane proteins, in high yield and high purity by cultivating the transformed yeast.

TECHNICAL BACKGROUND AND PRIOR ART

In developed countries, populations having immunity against HSV have recently decreased, and hence, they are experiencing serious problems in the increase of HSV infections such as herpes genetalis, neonatal herpes infection and herpes encephalitis in these countries. In order to prevent such HSV infections, vaccination is useful, and some vaccines have already been proposed such as an attenuated vaccine comprising attenuated HSV and an inactivated vaccine containing HSV DNA. It is known, however, that associated with HSV are problems such as latent infection and carcinogenicity, and the conventional attenuated vaccine and inactivated vaccine possess such side effects and hence are not preferable nor practical.

Cells infected by HSV produce several glycoproteins (e.g. gA, gB, gC, gD, gE, etc., the nomenclature of gA and gB has been standardized as "gB" by the International Herpes Virus Workshop (Oxford, England) in 1983). Since it has been found that these glycoproteins function as antigens for eliciting an immune response to inhibit HSV infection, various studies have been done on component vaccines comprising these glycoproteins. For instance, Cappel et al. have reported that glycoproteins extracted from HSV-infected cells or virus particles are effective as antigens for preventing infection by HSV (cf. Cappel et al., Arch. Virol., 73, 61, 1982). However, the component vaccine comprising glycoproteins extracted from HSV-infected cells or virus particles contains many proteins originated from the host cells and hence side effects due to the extra proteins are problematic. In order to obtain a suitable component vaccine having no side effects, it is necessary to obtain highly purified glycoproteins. The present inventors directed their research at the gB glycoprotein and have experimentally confirmed that their highly purified gB is a very effective antigen as demonstrated by experimentation in mice [cf. Kino, Cellular Technology, 3, 120 (1984).

Glycoprotein gB is usually produced by inoculating a virus into culture cells and then culturing the cells. However, this method is troublesome because it requires the handling of infectious material and involves complicated steps, and further, it is impossible to confirm the complete removal of viral DNA carrying a carcinogenic gene. Thus, it is very difficult to produce a safe component vaccine from natural glycoprotein gB.

The present inventors have found that the desired HSV proteins (i.e. HSVgB) could be produced by a genetic engineering technique, that is, by isolating the HSVgB gene and recombining the isolated HSVgB gene into a specific plasmid vector containing a yeast DNA sequence and an *E. coli* DNA sequence, wherein said vector contains the expression control region of the repressible acid phosphatase gene of yeast. The HSVgB gene is inserted under the control of the phosphatase promoter and yeast is transformed therewith and cultured to obtain the desired product. (cf. Japanese Patent Application Nos. 151766/1984 and 262465/1984, U.S. Ser. No. 755,776, European Patent Application No. 85109042.3 and Canadian Patent Application No. 487034).

The process disclosed in the above applications can produce very pure HSVgB suitable for the preparation of a vaccine, but it is still desirable to develop an improved process suitable for the production of the desired HSVgB in higher yield.

SUMMARY OF THE INVENTION

The present inventors have found that the desired HSVgB can be produced in higher yield by recombining a specific HSVgB gene, i.e. a herpes simplex virus gene having an N-terminal portion of the gene removed including a DNA sequence encoding the so-called signal sequence, into the vector as mentioned hereinbefore to prepare a recombinant plasmid, transforming a yeast therewith and then culturing the transformed yeast thus obtained.

An object of the present invention is to provide an improved recombinant plasmid which comprises a herpes simplex virus gB gene having an N-terminal portion of the gene deleted including a DNA sequence encoding the signal sequence. The modified HSVgB gene is inserted downstream of the promoter region of a plasmid vector containing a yeast DNA sequence and an *E. coli* DNA sequence such that it is under the control of said promoter. Another object of the invention is to provide a transformed yeast obtained by transforming a yeast with the recombinant plasmid as set forth above. A further object of the invention is to provide a process for the production of the desired HSVgB by culturing the transformed yeast. These and other objects and advantages of the invention will be apparent to those skilled in the art from the following description.

DETAILED DESCRIPTION OF THE INVENTION

Figure 1:
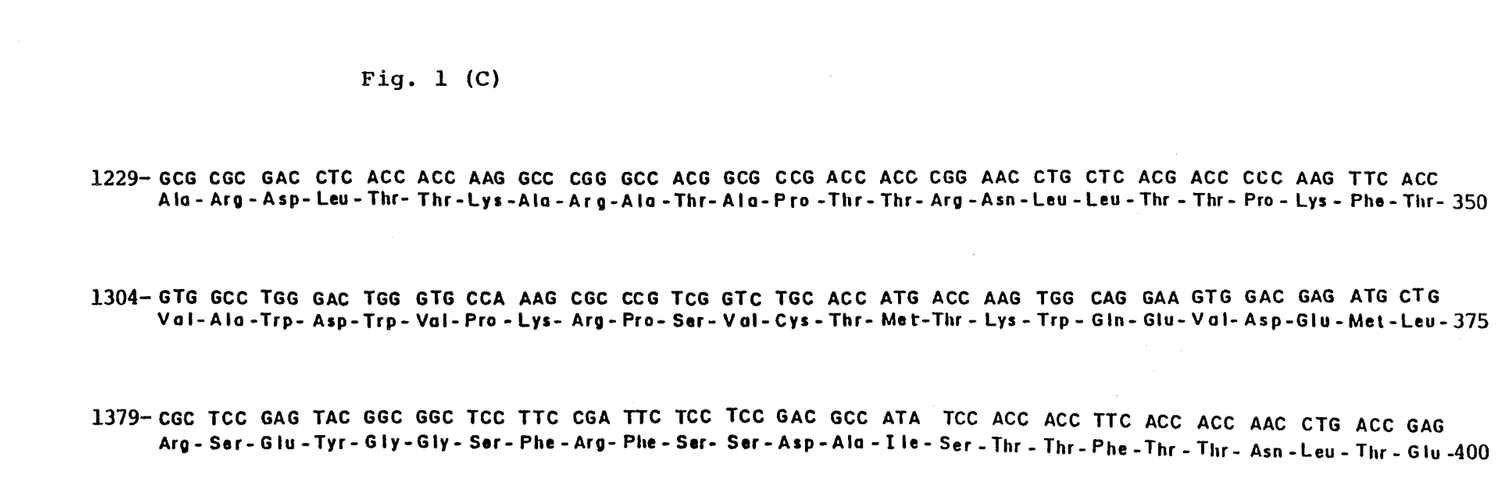
FIG. 1, parts A, B, and C, shows the base sequence of the HSVgB gene used in the present invention.

The HSVgB gene has a base sequence as shown in FIG. 1 which is also disclosed in the above-mentioned patent applications. In the base sequence, the N-terminal portion may be the DNA sequence encoding the so-called signal sequence which consists of 30 amino acids (in the figure, the underlined region). According to the present invention, by using an HSVgB gene fragment where the DNA sequence encoding the N-terminal 30 amino acids is removed, or an HSVgB gene fragment where the above-mentioned region and a region further downstream therefrom are removed (for instance, an HSVgB gene fragment from which a DNA sequence encoding the N-terminal 83 amino acids which can be cleaved by Nae I has been deleted, or an HSVgB gene fragment from which a DNA sequence encoding the N-terminal 320 amino acids which can be cleaved by Sal I has been deleted), a plasmid is constructed by recombining said HSVgB gene fragment into a shuttle vector under the control of a yeast promoter. A yeast is transformed with the prepared recombinant plasmid, and then the transformed yeast is cultured to produce the desired HSVgB protein having antigenicity and immunogenicity in a high yield.

The plasmid vector suitable for the recombination of the herpes simplex virus gene lacking the DNA sequence encoding the signal sequence is, for example, a vector containing a yeast DNA sequence and an E. coli DNA sequence and containing the expression control region of the repressible acid phosphatase gene of yeast, and further includes other plasmid vectors carrying other promoters having similar functions.

The recombinant plasmid of this invention, transformation of a yeast with said plasmid, and the production of HSVgB therewith are explained in more detail below.

(1) shuttle vector

In the present invention, the herpes virus gB gene lacking a DNA sequence encoding the signal sequence is recombined into a shuttle vector being replicable in both yeast and E. coli and carrying a promoter which can control expression of HSVgB, wherein the HSVgB gene is inserted downstream of the promoter region as mentioned hereinbefore.

The suitable shuttle vector used in the present invention is a plasmid vector which contains both a yeast DNA sequence and an E. coli DNA sequence and contains the repressible acid phosphatase gene of yeast, e.g. Saccharomyces cerevisiae, and the shuttle vector is constructed in the manner as disclosed below.

The yeast DNA sequence contains a DNA sequence which is necessary for replication of a plasmid in yeast independently from the chromosome, for instance, a DNA sequence necessary for replication of yeast (ars 1) and a DNA sequence necessary for the replication of 2 μm DNA (2 μ ori) and contains optionally a gene useful as a selective marker in the transformed yeast, for example, a leucine-producing gene, a histidine-producing gene, a tryptophane-producing gene, a uracil-producing gene, an adenine-producing gene, or the like, which may be used alone or in combination of two or more thereof.

The E. coli DNA sequence contains a DNA sequence necessary for the replication of the plasmid within cells of E. coli, for example, a DNA sequence of a replication initiating region of plasmid Col EI, and preferably contains a gene useful as a selective marker of the transformed E. coli. The selective marker includes, for example, an ampicillin-resistance gene, a kanamycin-resistance gene, tetracycline-resistance gene, chloramphenicol-resistance gene, or the like, which may be used alone or in combination of two or more thereof. Commonly used E. coli DNA is derived from pBR322 which contains an ampicillin resistance gene and tetracycline-resistance gene.

The shuttle vector used in the present invention is characteristic in that it contains the repressible acid phosphatase promoter of yeast. This acid phosphatase promoter is usually a polypeptide of 60,000 dalton (P60) which contains the phosphatase gene.

Suitable examples of the shuttle vector are produced from shuttle vector pAT 77 wherein a yeast DNA sequence containing ars 1, 2μ ori and a leucine-producing gene (Leu 2) is combined with E. coli plasmid pBR322, i.e. by treating the shuttle vector pAT 77 with an exonuclease Bal 31 to delete a part or whole of the structural gene of acid phosphatase and further optionally various regions upstream from the phosphatase gene up to $-100$ bp, preferably from $+1$ to $-50$. A representative example is shuttle vector pAm 82 wherein upstream to $-33$ bp is deleted. The method for the production of these shuttle vectors is disclosed in Japanese Patent First Publication No. 31799/1984. The shuttle vectors pAT 77 and pAM 82 carried in Saccharomyces cerevisiae (i.e. Saccharomyces cerevisiae AH 22/pAT 77 and Saccharomyces cerevisiae AH 22/pAM 82 respectively) have been deposited at Fermentation Research Institute, Agency of Industrial Science and Technology, Japan under the Budapest Treaty as "FERM BP-324" and "FERM-BP-313," respectively.

The shuttle vector pAM 82 has an Xho I site downstream of the acid phosphatase promoter and also a Pvu II site further downstream therefrom. In order to insert the HSVgB gene of this invention into the vector, pAM 82 is cleaved with the restriction enzyme Pvu II to create flush ends, and a BamHI linker is bound to this site, and the combined fragment is re-cyclized to form a plasmid pONY1. This plasmid pONY1 can express a foreign gene in pure form under the control of the acid phosphatase promoter, and the site to be recombined can readily be cleaved by treating it with restriction enzymes BamHI and Xho I, and hence, this shuttle vector is suitable for recombining genes as required.

(2) Production of HSVgB gene-containing fragments

As to the gB gene of HSV (KOS strain: P.S.E.B.M., 1964, Vol. 115), the position on the virus DNA (0.348–0.366 map units) and the base sequence have been determined by Bjik et al. [cf. David J. Bjik et al., Virology, 133, 301–314 (1984)].

The HSVgB gene to be inserted in to a shuttle vector in the present invention is present in a fragment having about 8 kb (0.345–0.399 map units) which is obtained by treating HSV DNA with the restriction enzyme BamHI, said fragment being hereinafter referred to as the "BamHI-G fragment."

The HSVgB-containing fragments can be prepared by cleaving HSV DNA with BamHI, and cloning the thus cleaved BamHI-G fragment as follows.

Figure 2:
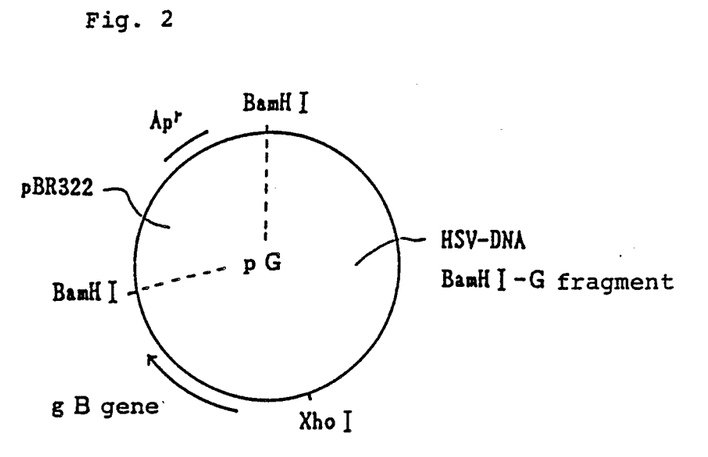
FIG. 2 shows a structure of plasmid pG containing BamHI-G fragment of HSV DNA used in the present invention.

Virus DNA is isolated from HSV which has been grown on Vero cells, and the virus DNA is cleaved with the restriction enzyme BamHI, and then the resulting BamHI-G fragment is isolated and extracted by subjecting to agarose gel electrophoresis. The BamHI-G fragment is ligated in the presence of $T_4$ ligase with E. coli plasmid pBR322 which is previously treated with BamHI. E. coli X1776 is transformed with the above reaction mixture. Among the transformants thus obtained, a strain having ampicillin resistance (Ap$^r$) and tetracycline sensitivity (Tc$^s$) is selected and is amplified, by which there is obtained a plasmid pG which contains the BamHI-G fragment. This plasmid pG has a structure as shown in the accompanying FIG. 2.

Figure 3:
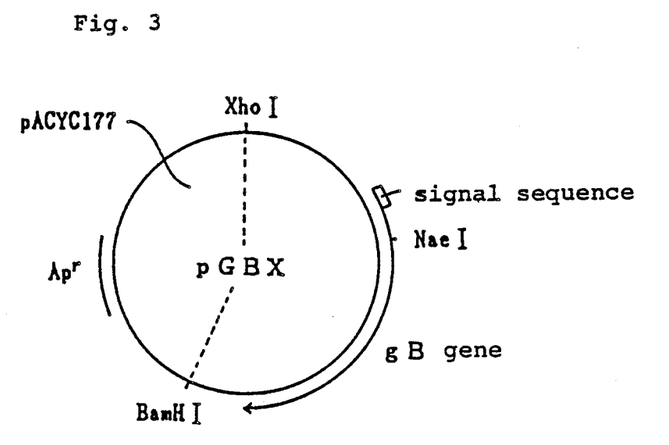
FIG. 3 shows a structure of plasmid pGBX containing the HSVgB gene having a signal sequence-encoding region used in the present invention.

The plasmid pG thus obtained is cleaved with both BamHI and Xho I to give a fragment (3.5 kb) containing the HSVgB gene. The fragment thus obtained is isolated by extraction and then is ligated in the presence of $T_4$ ligase with a fragment (2.6 kb) of *E. coli* pACYC177, which was obtained by previous treatment with BamHI and Xho I. *E. coli* is transformed with the above reaction mixture, and the resulting transformant having ampicillin resistance is amplified, and then a plasmid pGBX containing the HSVgB gene is obtained from the amplified cells. This plasmid pGBX has a structure as shown in the accompanying FIG. 3.

(3) Construction of HSVgB gene-expression plasmid

As is mentioned hereinbefore, the present invention provides a recombinant plasmid obtained by recombining an HSVgB gene fragment lacking a region encoding the signal sequence of the HSVgB gene or an HSVgB gene fragment lacking a region encoding said signal sequence and a portion of the downstream region therefrom into a shuttle vector, and by using the recombinant plasmid, a herpes simplex virus protein suitable for the production of a vaccine effective for the prophylaxis of herpes simplex virus infections can be produced. The HSVgB gene-expression plasmid can be constructed from the above plasmid pGBX by removing various regions containing DNA encoding a signal sequence, the length of the sequence depending on the cleavage sites by restriction enzymes of the HSVgB gene as follows.

Figure 4:
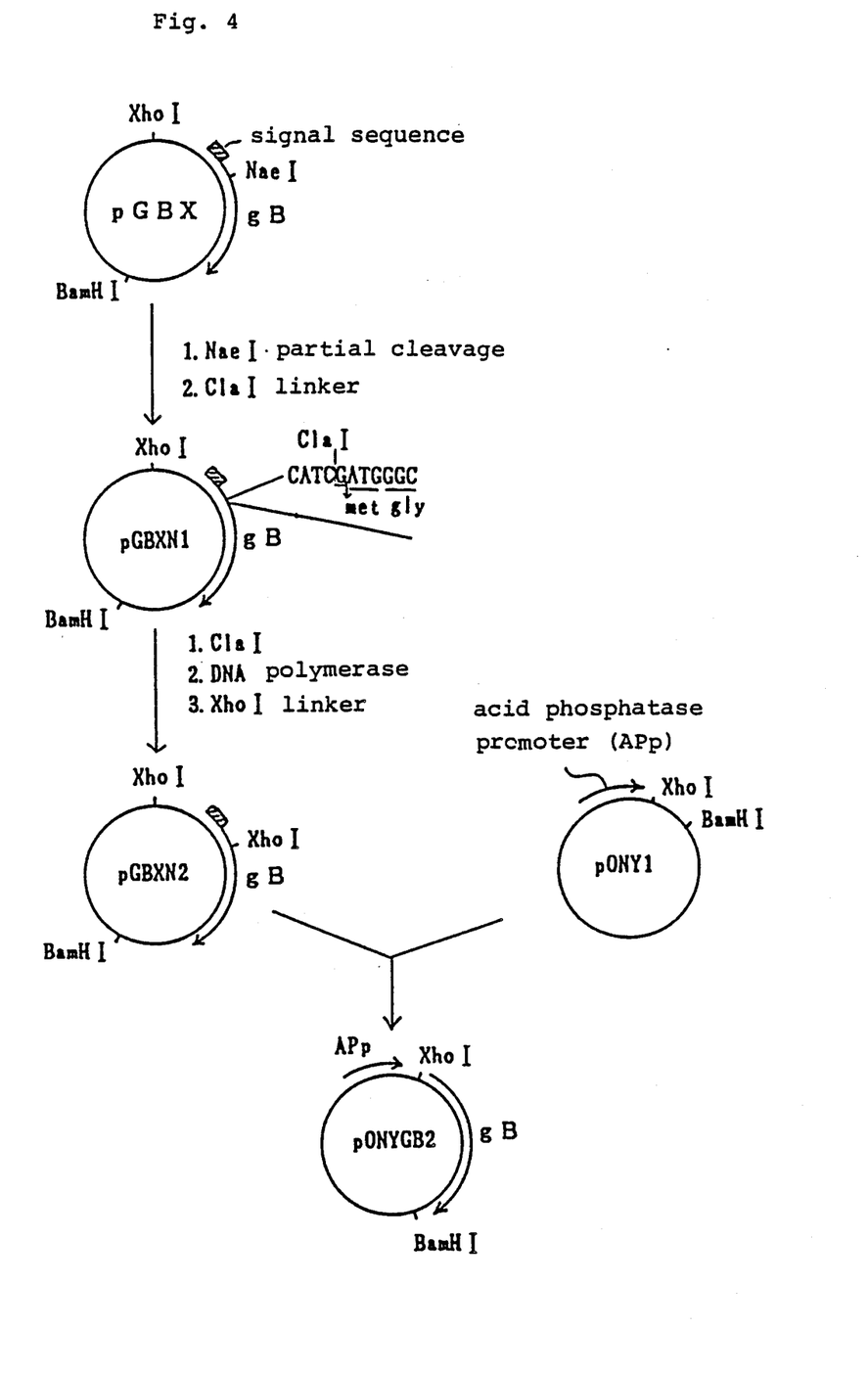
FIG. 4, FIG. 5 and FIG. 6 show steps for the construction of various recombinant plasmids from the plasmid pGBX by the present invention.

(a) Deleting a DNA sequence encoding the N-terminal 83 amino acids (cf. FIG. 4):

First, the plasmid pGBX is partially cleaved with a restriction enzyme Nae I and thereto is bound a Cla I linker (CATCGATG) with $T_4$ ligase and then the plasmid is re-cyclized. A plasmid is selected wherein only the Nae I site corresponding to the 83rd amino acid from the N-terminal methionine is converted into a Cla I site (this plasmid is hereinafter referred to as "plasmid pGBXN1"). By this procedure, the methionine-coding ATG is added directly upstream of the 84th amino acid from the N-terminal methionine of gB.

The plasmid pGBXN1 obtained above is cleaved with the restriction enzyme Cla I and flush ends are formed with DNA polymerase, and thereto is bound an Xho I linker with $T_4$ ligase and then the plasmid is re-cyclized. The thus obtained plasmid (referred to as "pGBXN2") has a structure in which the Cla I site of the plasmid pGBXN1 is exchanged with a Xho I site.

The plasmid pGBXN2 is cleaved with Xho I and BamHI, and from the resulting fragments, a fragment (2.9 kb) containing no gB signal sequence-coding region is selected and is bound using $T_4$ ligase with the shuttle vector pONY1, which is previously treated with Xho I and BamHI, to give the desired plasmid recombined with an HSVgB gene fragment lacking a region encoding the signal sequence downstream of the acid phosphatase promoter (the plasmid is hereinafter referred to as "pONYGB2").

Figure 5:
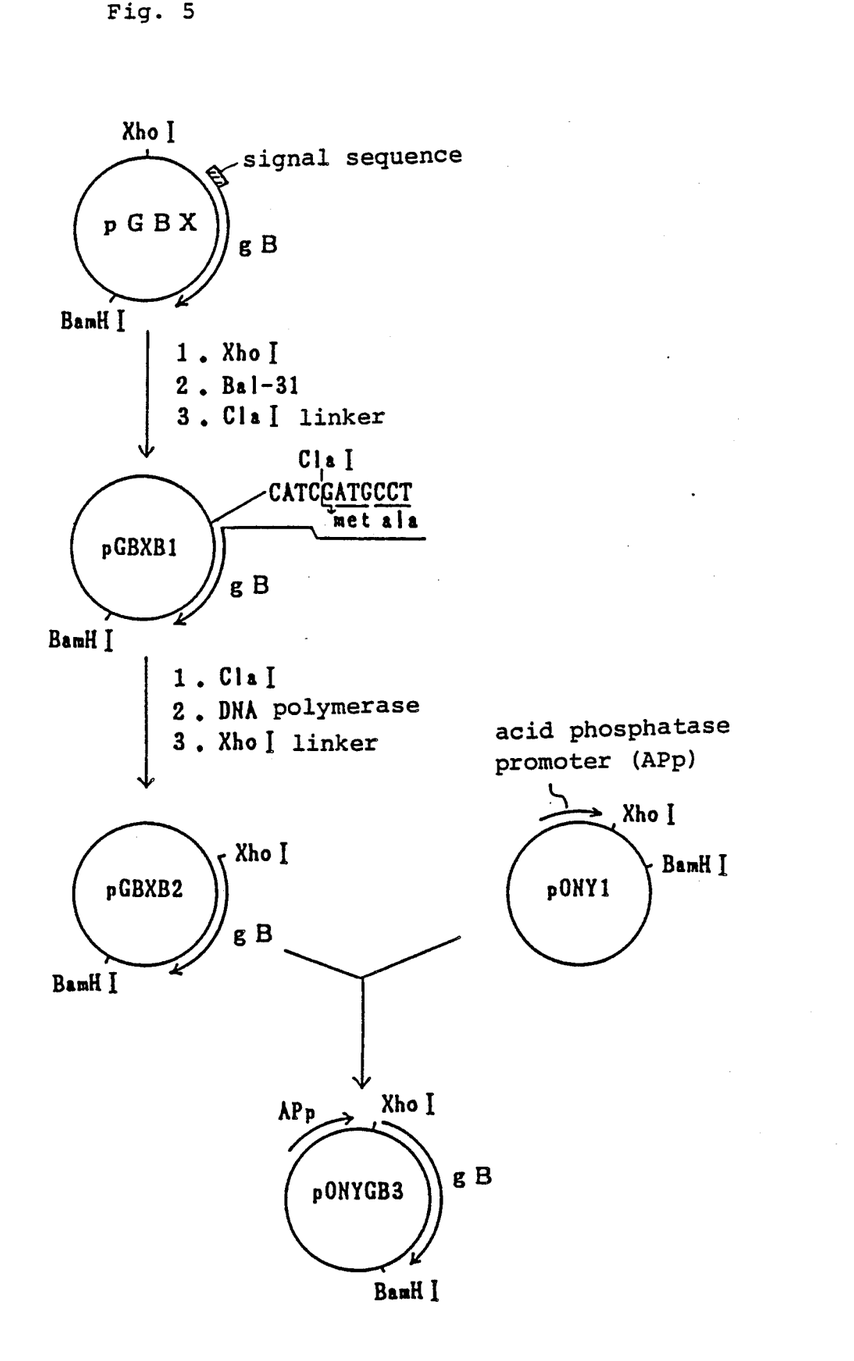
Figure 6:
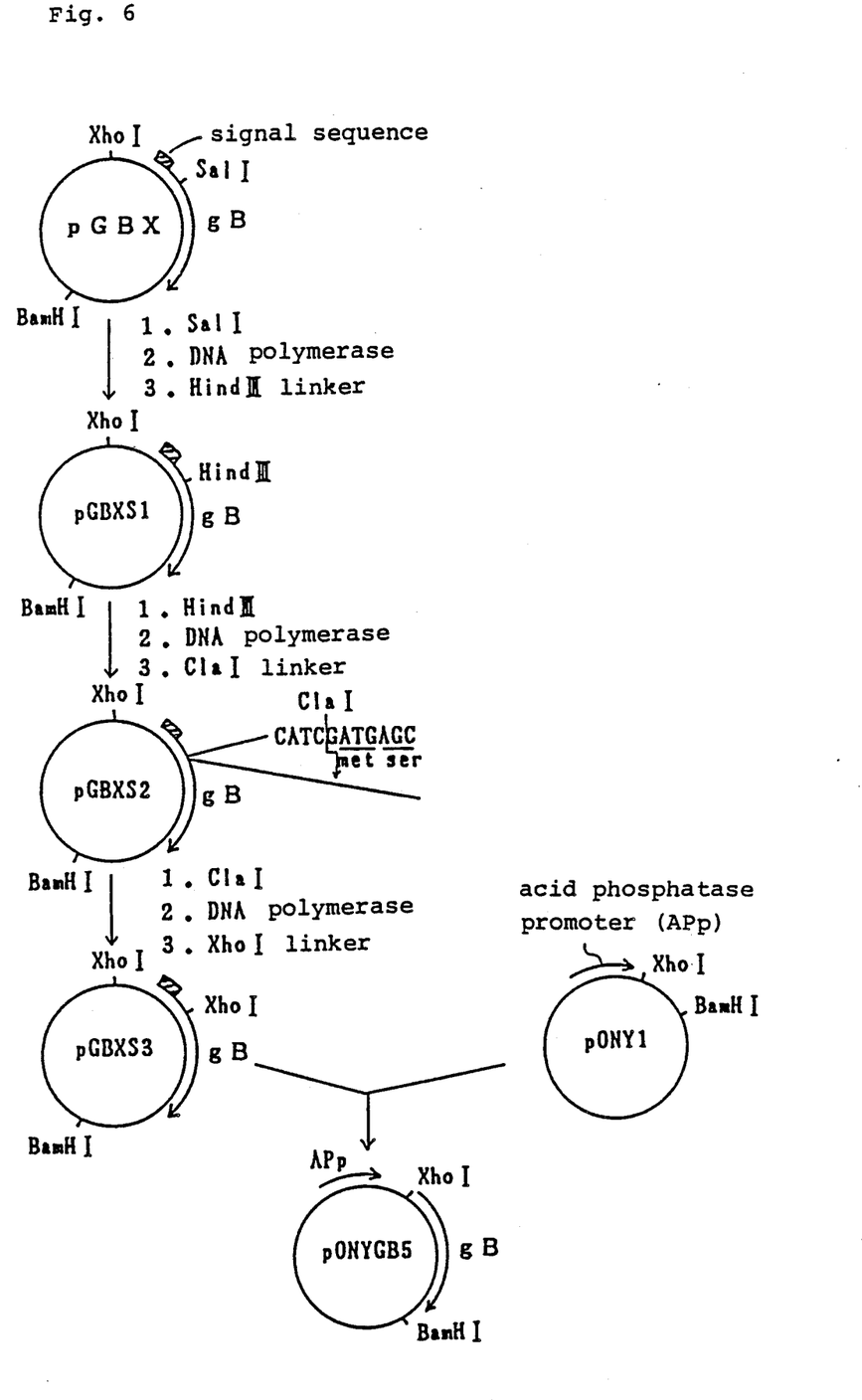

(b) Deleting a DNA Sequence encoding the N-terminal 30 amino acids (signal sequence-encoding region) (cf. FIG. 5);

The plasmid pGBX is cleaved with the restriction enzyme Xho I, and in order to remove the signal sequence of gB gene, it is then treated with exonuclease Bal 31. The DNA treated with Bal 31 is bound with a Cla I linker (CATCGATG) using $T_4$ ligase and then re-cyclized. A plasmid is selected (hereinafter referred to as "pGBXB1") wherein the region encoding the signal sequence of gB gene is removed and further the ATG of the inserted Cla I linker is in the same frame as the codon encoding the amino acid of the gB gene downstream therefrom.

The plasmid pGBXB1 obtained above is cleaved with the restriction enzyme Cla I and flush ends are formed with DNA polymerase, and thereto is bound an Xho I linker (CCTCGAGG) with $T_4$ ligase and then the plasmid is re-cyclized. The thus obtained plasmid (referred to as "pBGXB2") is cleaved with Xho I and BamHI, and 3 Kb DNA fragment containing the gB gene is isolated and then subjected to binding using $T_4$ ligase with the shuttle vector pONY1, which is previously treated with Xho I and BamHI, to give the desired plasmid inserted with the gB gene downstream of the acid phosphatase promoter (the plasmid is hereinafter referred to as "pONYGB3").

(c) Deleting a DNA sequence encoding the N-terminal 320 amino acids:

The plasmid pGBX is cleaved with the restriction enzyme Sal I and flush ends are formed with DNA polymerase, and thereto is bound a Hind III linker (ACAAGCTTGT) using $T_4$ ligase and then the plasmid is re-cyclized. The thus prepared plasmid (referred to as "pGBXS1") is cleaved with Hind III and flush ends are formed with DNA polymerase and is bound with a Cla I linker (CATCGATG) using $T_4$ ligase and then the plasmid is re-cyclized. In the thus prepared plasmid (referred to as "pGBXS2"), the ATG of the inserted Cla I linker is in the same frame as the codon encoding the amino acid of the gB gene downstream therefrom.

The plasmid pGBXS2 obtained above is cleaved with the restriction enzyme Cla I and flush ends are formed with DNA polymerase, and thereto is bound an Xho I linker (CCTCGAGG) with $T_4$ ligase and then the plasmid is re-cyclized. The thus obtained plasmid (referred to as "pBGXS3") is cleaved with Xho I and BamHI, and 2.2 kb DNA fragment containing the gB gene is isolated and then subjected to binding using $T_4$ ligase with the shuttle vector pONY1, which is previously treated with Xho I and BamHI, to give the desired plasmid inserted with the gB gene downstream of the acid phosphatase promoter (the plasmid is hereinafter referred to as "pONYGB5").

(4) Transformation of yeast

The yeast to be transformed includes a mutant strain of yeast which is complementary with the selective marker gene of the transformed yeast carried on the plasmid, for example, a leucine-requiring mutant, *Saccharomyces cerevisiae* AH 22 [a, leu 2, his 4, Can 1 (cir+)] (cf. Hinnen, A. et al., Proc. Natl. Acad. Sci., U.S.A., 75, 2157–2161, 1978) or *Saccharomyces cerevisiae* AH 22 pho 80 [a, leu 2, his 4, Can 1 (Cir+)] (cf. Thoe, A. et al., J. Bacteriol., 145, 221–232, 1981). After amplifying in *E. coli*, the recombinant plasmid is applied to the mutant strain of yeast in a usual manner, for example, by mixing the plasmid DNA with cells obtained by conversion into spheroplasts, followed by treatment of the cells with calcium by which the transformation is effected. The desired transformed yeast is selected and isolated from the yeast culture thus treated based on the expression of a gene complementary with the mutation of the host yeast carried on the vector, for example, expression of a leucine-producing gene.

In addition to the above-mentioned leucine-requiring strain, various other mutant strains such as a histidine-requiring strain, tryptophane-requiring strain, uracil-requiring strain, adenine-requiring strain, or the like can be used as the yeast.

(5) Culture of transformed yeast and production of HSVgB

The transformed yeast obtained above is cultured in a medium containing phosphoric acid in a usual manner, and the culture cells in logarithmic growth phase are transferred to an inorganic phosphate free medium and are cultured in said medium such that the acid phosphatase promoter is not repressed. After culturing, the produced cells are collected and lysed in a usual manner to give a lysed cell solution containing a large amount of the desired HSVgB protein.

Depending on the kind of yeast, for instance, when pho 80 mutant strain is used, culturing is not necessarily required to be carried out under the conditions that the acid phosphatase promoter is not repressed, but may be done under usual conditions to directly give the desired HSVgB protein in a large amount.

The HSVgB protein can be purified by conventional purification methods. For instance, the protein-containing solution is passed through a column packed with a gel bound with an anti-gB antibody, and then the adsorbed gB is eluted with 3M KSCN.

The gB thus obtained has the same immunological properties as those of natural gB obtained from HSV-infected cells and can be used for the preparation of an HSV vaccine and diagnostic reagents.

The recombinant DNA, transformed yeast, and the production of the HSVgB protein of the present invention are illustrated by the following example, but should not be construed to be limited thereto.

EXAMPLE (1) Preparation of DNA containing the HSVgB gene:
(i) Preparation of HSV-1 DNA:

Vero cells (about $5 \times 10^8$ cells) are infected with 0.5-1 PFU/cell of HSV type 1 (HSV-1) KOS strain and the cells are cultured at 37° C. for 20-24 hours. The culture mixture is then centrifuged at 23,000 r.p.m. for 1 hour to separate the infected cells and the supernatant, and thereby pellets of infected cells (2-3 ml) are isolated. The pellets are suspended in a phosphate buffered saline solution (hereinafter, referred to as "PBS") (pH 7.2, 6 ml). The suspension is subjected to ultrasonic treatment (9 KHz, 200 W, for 5 minutes) or to freezing-thawing [repeating three times freezing at $-50°$ C. (with acetone-dry ice) and thawing at 37° C.] to fracture the cells, and the cell residue is removed by centrifugation at low speed (3,000 r.p.m., 20 minutes). The solution thus obtained is layered on glycerol cusion (5%, 40%) and then centrifuged at 35,000 r.p.m. for one hour. The pellets (0.5-1 ml) thus obtained are suspended in PBS (1-2 ml) and are treated with DNase (10 µg/ml) and RNase (0.3 mg/ml) at 37° C. for one hour, and to the reaction mixture is added 1/5 volume of 5×STEP [a mixture of 0.5% SDS (sodium dodecylsulfate), 50 mM Tris-HCl (pH 7.5), 0.4M EDTA, and 0.1% proteinase K], and the mixture is reacted at 50° C. for 30 minutes. The resulting solution is extracted with an equivolume of phenol, phenol-chloroform (1:1) and chloroform in this order to give an aqueous layer containing DNA.

The aqueous layer is dialyzed against TE buffer (20 mM Tris-HCl, 1 mM EDTA, pH 7.5), and thereto is added cold ethanol to precipitate the DNA. The DNA is separated by filtration, dried in vacuum, and then dissolved in an aqueous cesium chloride [Rf 1.3885, incorporated with ethidium bromide (0.04%) and lauroyl sarcosinate (0.4%), 5 ml]. The mixture is centrifuged at 4,000 r.p.m. for 72 hours to form a band of HSV-1 DNA. The band is recovered and is washed with isopropyl alcohol to remove ethidium bromide, and then dialyzed against TE buffer. Cold ethanol is added thereto to precipitate HSV-1 DNA.

(ii) Cloning of BamHI-cleaved G fragment of HSV-1 DNA:

The HSV-1 DNA obtained above (about 100 µg) is treated with the restriction enzyme BamHI in a mixture (0.75 ml) of 73 mM Tris-HCl (pH 8.0), 7 mM MgCl$_2$, 100 mM NaCl and 2 mM 2-mercaptoethanol at 37° C. for 6 hours, and the treated DNA is subjected to 0.7% agarose electrophoresis for separation of fragments such that a portion of the gel is cut out corresponding to the G fragment (0.345-0.399 map units), and from which the G fragment is electrophoretically recovered.

E. coli pBR322 plasmid (1/10 mole) which is obtained by cleaving with the restriction enzyme BamHI in the same manner as described above is reacted with the above G fragment (about 2 µg) in a mixture of 50 mM Tris-HCl (pH 7.9), 10 mM MgCl$_2$, 20 mM dithiothreitol and 1 mM ATP by using T$_4$ DNA ligase at 16° C. for about 16 hours.

The above reaction mixture is added to a suspension of E. coli (0.1 ml) which is prepared by treating a culture broth of E. coli X1776 (cf. Curtiss, R. III, "Molecular Cloning of Recombinant DNA" ed. Scott, W. A. and Werner, R., page 99, Academic Press, 1977) by the procedure as described in Norgard, M. V., Gene, 3, 279 (1978), and the mixture is mixed well and allowed to stand at 0° C. for 45 minutes. The mixture is applied onto an agar plate containing ampicillin (100 µg/ml) and then incubated at 37° C. overnight. The resulting colonies are applied onto both an agar plate containing ampicillin (100 µg/ml) and an agar plate containing tetracycline (100 µg/ml), and are incubated likewise. The colonies which grow only on the agar plate containing ampicillin are selected. pBR322 has an ampicillin-resistant gene and a tetracycline-resistant gene, but when it is inserted with HSV-1 DNA fragment at the BamHI site of the tetracycline-resistant gene, it loses the tetracycline-resistance. Accordingly, the selected colonies contain a recombinant DNA of BamHI-G fragment of pBR322-HSV DNA.

From the colonies thus selected, a plasmid is prepared by the procedure as described by K. Matsubara (J. Virol., 16, 479, 1975). The plasmid thus prepared is subjected to cleavage pattern analysis by treating with various restriction enzymes (e.g. BamHI, Bst EII, Kpn I, Sal I, Sst I, Xho I) to obtain a recombinant DNA of pBR322-BamHI-G fragment wherein the BamHI-G fragment of HSV-1 DNA is inserted into pBR322 (hereinafter, referred to as "plasmid pG").

(iii) Preparation of plasmid pGBX:

The plasmid pG (10 µg) obtained in the above (ii) is added to a mixture (100 µl) of 6 mM Tris-HCl (pH 7.5), 6 mM MgCl$_2$, 6 mM 2-mercaptoethanol and 150 mM NaCl, and thereto are added restriction enzymes BamHI (10 units) and Xho I (10 units), and the mixture is reacted at 37° C. for 2 hours. 3.5 kb fragment DNA is isolated from the reaction mixture by 1% agarose gel electrophoresis in accordance with the method disclosed by Yasusuke Takagi, "Manual for Procedure of Genetic Engineering," pages 33-34, and the 3.5 kb fragment DNA (100 ng) is reacted with E. coli plasmid pACYC 177 (which is cleaved with BamHI and Xho I) (10 ng) in a mixture (10 μl) of T4 ligase (0.1 unit), 6.6 mM MgCl2 and 10 mM dithiothreitol at 16° C. for 8 hours. By using the above reaction mixture, E. coli X1776 is transformed in the same manner as described hereinbefore, and ampicillin resistant cells are selected from the resulting transformants. From the cells thus selected, a plasmid pGBX containing gB gene is prepared by the procedure as described by K. Matsubara (J. Virol., 16, 479, 1975).

(iv) Preparation of plasmid pGBXN2:

The above plasmid is treated in the following manner, whereby only the Nae I site at about 250 bp downstream from the gB gene translation initiation codon ATG is converted into a Cla I site.

The plasmid pGBX (2 μg) is treated with Nae I (0.1 unit) in a mixture of 6 mM Tris-HCl (pH 7.5), 50 mM NaCl, 6 mM MgCl2 and 6 mM 2-mercaptoethanol and the mixture is subjected to precipitation with ethanol. The DNA thus obtained is added to a mixture (50 μl) of T4 DNA polymerase (0.1 unit), 200 μM dATP, dCTP, dGTP, dTTP, 67 mM Tris-HCl (pH 8.6), 6.7 mM MgCl2, 10 mM 2-mercaptoethanol, and 16.7 mM (NH4)2SO4, and the mixture is reacted at 37° C. for 30 minutes and then subjected to treatment with phenol and precipitation with ethanol. The DNA thus obtained (1 pmole) is added to a mixture (10 μl) of T4 ligase (0.1 unit), 66 mM Tris-HCl (pH 7.6), 6.6 mM MgCl2, 10 mM dithiothreitol, 66 μM ATP and 10 pmole Cla I linker (CATCGATG), and the mixture is reacted at 16° C. for 8 hours.

E. coli X1776 is transformed with the reaction mixture obtained above in the same manner as described hereinabove. Clones growing on an ampicillin-containing plate are selected, and plasmids are prepared from the selected cells in the same manner as described above. The plasmids are treated with restriction enzymes Cla I and BamHI, and thereby there is selected the desired plasmid pGBXN1 as determined by the patterns in electrophoresis. In the plasmid pGXN1, only the Nae I site downstream of the translation initiation codon ATG of the gB gene is converted into the Cla I site.

The plasmid pGBXN1 (2 μg) obtained above is treated with Cla I (2 units) in a mixture (50 μl) of 6 mM Tris-HCl (pH 7.9), 50 mM NaCl, 6 mM MgCl2 and 6 mM 2-mercaptoethanol at 37° C. for one hour. The reaction mixture is subjected to treatment with phenol and precipitation with ethanol. The DNA thus obtained is treated with T4 polymerase and further with an Xho I linker (CCTCGAGG) in the same manner as described above. From the plasmids thus obtained, there is selected the desired plasmid pGBXN2 wherein the Cla I site is converted into an Xho I site.

(2) Preparation of shuttle vector pONY1:

Shuttle vector pAM 82 as prepared in the same manner as described in Japanese Patent First Publication No. 31799/1984 is treated as follows in order to convert the Pvu II site into BamHI site.

A fragment (2 μg) prepared by cleaving the plasmid pAM 82 with Xho I is reacted with T4 DNA polymerase (0.1 unit) in a mixture (50 μl) of 67 mM Tris-HCl (pH 8.6), 6.7 mM MgCl2, 10 mM 2-mercaptoethanol, 6.7 μM EDTA and 16.7 mM (NH4)2SO4 which contains 200 μM dATP, dCTP, dGTP and dTTP at 37° C. for 30 minutes. The reaction mixture is subjected to phenol extraction and ethanol precipitation. The resulting DNA is reacted with a BamHI linker in a molar ratio of 1:10 by using T4 ligase at 16° C. for 8 hours.

E. coli X1776 is transformed with the reaction mixture obtained above in the same manner as described hereinbefore. The ampicillin-resistant cells thus obtained are incubated, and from the cells thus obtained, there is isolated a plasmid pONY1 in the same manner as described hereinbefore. In said plasmid pONY1, the Pvu II site of pAM 82 is converted into a BamHI site.

(3) Preparation of HSVgB gene expression plasmid:

The plasmid pGBXN2 (10 μg) containing the HSVgB gene as prepared above is reacted with BamHI (10 units) and Xho I (10 units) in a mixture (100 μl) of 6 mM Tris-HCl (pH 7.5), 6 mM MgCl2, 6 mM 2-mercaptoethanol and 150 mM NaCl at 37° C. for 2 hours. From the reaction mixture, a DNA fragment (2.9 kb) is isolated by 1% agarose electrophoresis containing the HSVgB gene from which the signal sequence-encoding region has been deleted.

Separately, the shuttle vector pONY1 (10 μg) obtained in the above (2) is treated with restriction enzymes BamHI and Xho I in the same manner as described hereinbefore, and from the reaction mixture, a DNA fragment is isolated by 1% agarose electrophoresis (10 kb) containing the acid phosphatase promoter.

The 2.9 kb fragment (100 ng) and the 10 kb fragment (10 mg) obtained above are reacted with T4 ligase (0.1 unit) in a mixture (10 μl) of 66 mM Tris-HCl (pH 7.6), 6.6 mM MgCl2, 10 mM dithiothreitol and 66 μM ATP at 16° C. for 8 hours.

E. coli X1776 is transformed with the reaction mixture obtained above in the same manner as described hereinbefore. The ampicillin-resistant cells thus obtained are incubated, and from the cells thus obtained, there is isolated a recombinant plasmid pONYGB2, wherein the HSVgB gene from which the DNA sequence encoding the N-terminal 83 amino acids including the signal sequence-encoding region has been deleted, is inserted downstream of the acid phosphatase promoter in the same manner as described hereinbefore.

(4) Preparation of transformed yeast:

The starting yeast is Saccharomyces cerevisiae AH 22 [a, leu 2, his 4, can 1 (Cir+)], which has been deposited at Fermentation Research Institute, Agency of Industrial Science and Technology, Japan under Budapest Treaty as "FERM BP-312". The starting yeast is inoculated in YPD medium (100 ml) consisting of 2% polypeptone, 1% yeast extract and 2% glucose, and the mixture is incubated at 30° C. overnight, and thereafter, the cells are collected by centrifugation. The cells thus collected are washed with sterilized water (20 ml), suspended in a solution (5 ml) of 1.2M sorbitol and Zymolyase-60,000 (manufactured by Seikagaku Kogyo K. K., Japan, 100 μg/ml), and the suspension is allowed to stand at 30° C. for 30 minutes to yield spheroplasts. The spheroplasts thus prepared are washed with 1.2M sorbitol solution three times, and then suspended in a solution (0.6 ml) of 2M sorbitol, 10 mM CaCl2 and 10 mM Tris-HCl (pH 7.5). The suspension thus prepared is divided into a small test tube in a volume of 60 μl. To the suspension is added the solution of the recombinant plasmid pONYGB2 (10 μg) as prepared above (3). After mixing well, 0.1M CaCl2 (3 μl) is added thereto in a final concentration of 10 mM CaCl2, and the mixture is allowed to stand at room temperature for 5 to 10 minutes. To the resulting mixture is added each 1 ml of a solution of 20% polyethylene glycol 4,000, 10 mM CaCl2 and 10 mM Tris-HCl (pH 7.5), and the mixture is 
allowed to stand at room temperature for about 20 minutes. The resulting mixture (each 0.2 ml) is added to a medium (10 ml) consisting of 22% sorbitol, 2% glucose, 0.7% yeast nitrogen base amino acid, 2% YPD, 20 μg/ml histidine and 3% agar, which is kept at a constant temperature of 45° C. After gently mixing, the mixture is added in a layer onto a plate of minimal medium containing 1.2M sorbitol which is previously prepared and consists of 0.7% yeast nitrogen base amino acid, 2% glucose, 20 μg/ml histidine and 2% agar and is set thereon. The plate is incubated at 30° C. to yield colonies of non-leucine requiring yeast. A colony is incubated in a BurkHolder minimal medium supplemented with histidine (20 μg/ml) [cf. Tohe, A. et al; J. Bacterol., 113, 727–738, 1973] to give the desired transformed yeast: *Saccharomyces cerevisiae* YGBS.

(5) Production of HSVgB protein by the transformed yeast:

A colony of the transformed yeast obtained in the above (4) is applied onto an agar plate of BurkHolder minimal medium supplemented with histidine (20 μg/ml) and incubated at 30° C. to form a colony (in order to confirm the transformant requires no leucine). The resulting cells are separated from the colony, inoculated in BurkHolder minimal medium (10 ml) supplemented with histidine (20 μg/ml) and incubated at 30° C. After about 24 hours, the cells in logarithmic growth phase are collected by centrifugation and are suspended in a minimal medium (10 ml) containing no phosphoric acid (which is prepared by replacing $KH_2PO_4$ in BurkHolder minimal medium with KCl, followed by supplementing 20 μg/ml histidine) in a cell concentration of about $4\times10^6$ cells/ml. After incubating at 30° C. for about 24 hours, the culture broth is centrifuged at 4,000 r.p.m. for 10 minutes to collect the cells. The cells thus separated are suspended in a solution (3 ml) of 1.2M sorbitol, 50 mM phosphate buffer (pH 7.2), 14 mM 2-mercaptoethanol and 100 μg/ml Zymolyase-60,000 (manufactured by Seikagaku Kogyo K. K., Japan), and the mixture is gently shaken at 30° C. for 30 minutes to yield spheroplasts. The spheroplasts are collected by centrifugation and are well suspended in 50 mM phosphate buffer (pH 7.2, 1 ml) containing 1% Triton X-100, and the mixture is vigorously stirred with glass beads to fracture the cells. The resulting suspension is centrifuged at 5,000 r.p.m. for 10 minutes, and the resulting supernatant is taken as the yeast-lysed solution. The gB antigen activity of the supernatant was measured by an enzyme immunoassay. The results are shown in Table 1. In Table 1, also shown is the value corresponding to yeast having shuttle vector pONY1 as a negative control and the value corresponding to gB purified from HSV as a positive control. As is clear from the table, the yeast transformed with the recombinant plasmid of the present invention effectively produces the desired HSVgB.

Additionally, the yeast-lysed solution obtained above (each 1 ml) was subcutaneously administered to guinea pigs (5 animals) four times every other week. As a result, there was observed neutralizing antibody in all guinea pigs, by which it was confirmed that the solution had gB immunogenicity.

For recombinant plasmids pONYGB3 and pONYGB5, similar results were obtained.

TABLE 1

| Run No. | 1 | 2 | 3 | 4 | 5 | 6 | 7 | 8 |
|---|---|---|---|---|---|---|---|---|
| gB activity ($OD_{492}$) | 0.75 | 0.62 | 0.70 | 0.87 | 0.67 | 0.66 | 0.01 | 0.45 |

[Note]:
Run Nos. 1-6: Yeast clone (TGBS) which was transformed by plasmid pONYGB2
Run No. 7: Yeast having plasmid pONYG1
Run No. 8: HSV-origin purified gB

What is claimed is:

1. A recombinant plasmid which comprises a plasmid vector containing DNA sequences necessary for replication of the yeast ars 1 and 2 μori and optionally a gene useful as a selective marker in transformed yeast, and a DNA sequence of a replication initiating region of plasmid col E1 and optionally a gene useful as a selective marker in transformed *Escherichia coli*, said vector being able to replicate in both *Escherichia coli* and yeast, said vector carrying a promoter region and a herpes simplex virus gB gene under control of the promoter, such that HSVgB protein coded for by said herpes simplex virus gB gene can be expressed in yeast, wherein a DNA sequence encoding the N-terminal 30 amino acids of the herpes simplex virus gB protein is deleted.

2. A recombinant plasmid which comprises a plasmid vector containing DNA sequences necessary for replication of the yeast ars 1 and 2 μori and optionally a gene useful as a selective marker in transformed yeast, and a DNA sequence of a replication initiating region of plasmid col E1 and optionally a gene useful as a selective marker in transformed *Escherichia coli*, said vector being able to replicate in both *Escherichia coli* and yeast, said vector carrying a promoter region and a herpes simplex virus gB gene under control of the promoter, such that HSVgB protein coded for by said herpes simplex virus gB gene can be expressed in yeast, wherein a DNA sequence encoding the N-terminal 83 amino acids of the herpes simplex virus gB protein is deleted.

* * * * *